United States Patent [19]

Voss

[11] Patent Number: 4,867,230

[45] Date of Patent: Sep. 19, 1989

[54] CONVECTION BLANKET WARMER

[76] Inventor: Gene Voss, 4227 Centergate, San Antonio, Tex. 78217

[21] Appl. No.: 180,245

[22] Filed: Apr. 11, 1988

[51] Int. Cl.4 ........................ A47C 27/08; A47C 27/10
[52] U.S. Cl. .......................................... 165/46; 5/284; 5/423; 5/469; 62/261; 128/376; 128/402
[58] Field of Search ...................... 165/46; 5/284, 423, 5/469; 128/399, 403, 376, 402; 62/261, 259.3

[56] References Cited

U.S. PATENT DOCUMENTS

| | | | |
|---|---|---|---|
| 2,504,308 | 4/1950 | Konkle . | |
| 2,512,559 | 6/1950 | Williams | 5/347 |
| 2,601,189 | 6/1952 | Wales | 4/160 |
| 2,617,915 | 11/1952 | Blair | 219/39 |
| 2,991,627 | 7/1961 | Suits . | |
| 3,486,177 | 12/1969 | Marshack | 5/347 |
| 3,602,001 | 8/1971 | Bauer et al. . | |
| 3,867,939 | 2/1975 | Moore et al. . | |
| 4,660,388 | 4/1987 | Greene, Jr. | 165/45 |

Primary Examiner—Albert W. Davis, Jr.
Attorney, Agent, or Firm—David G. Henry

[57] ABSTRACT

A convection blanket for warming persons lying thereon. The preferred embodiment has four layers, two outer insulating layers, and two inner layers of metallic foil. The inner metallic layers minimize heat loss across the length of the blanket. A unique pattern of pinholes in the top layers allows a larger volume of warm air to exit the blanket at the end opposite the air supply hose. All layers are stitched intermittently to avoid distension of the blanket, without defining clear channels, assuring uniform distribution of air within the blanket.

11 Claims, 1 Drawing Sheet

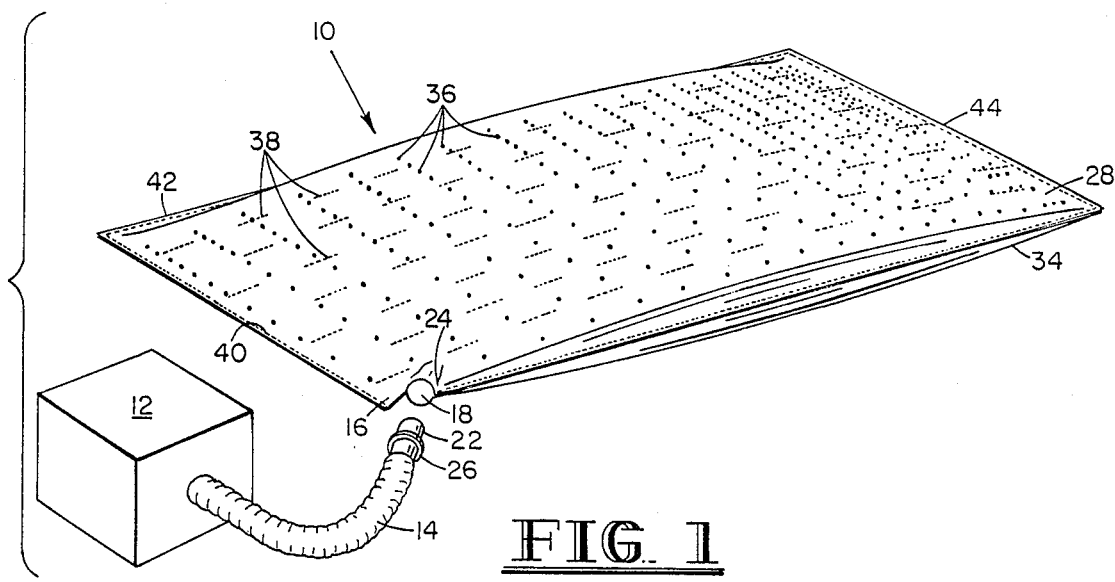
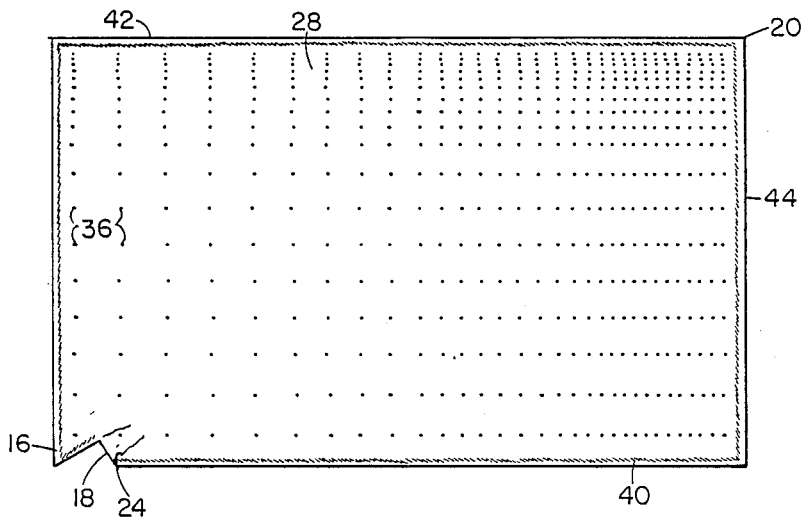
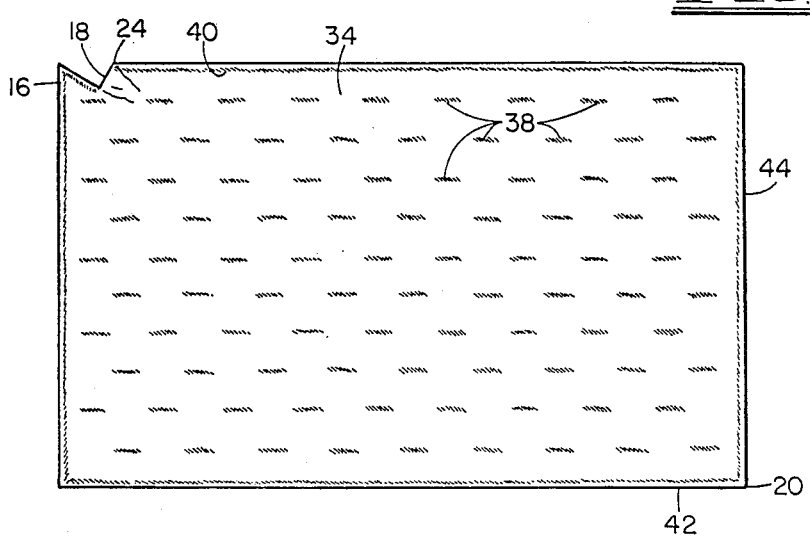
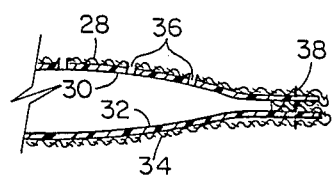

CONVECTION BLANKET WARMER

BACKGROUND OF THE INVENTION

1. Field of the Invention

The present invention generally relates to devices used to ventilate, cool, or warm persons, and more particularly to a blanket-type device which may be used to warm a body during surgical procedures.

2. Description of the Prior Art

Dozens of devices have been created to maintain a comfortable living environment for men and women. Air conditioning and heating systems for homes often meet this demand, but because of the expensive nature of such systems, and due to the fact that different individuals frequently have different desires concerning ambient conditions, several inventions have been devised to warm or cool smaller areas or spaces. A good example is an electrical heating pad, which may vary in size from about one square foot to the size of a bed, making it a heating blanket.

There have been several improvements on the idea of a heating/cooling blanket. One device, disclosed in U.S. Pat. No. 3,602,001 issued to Bauer et al., actually contemplates burning a fuel mixture within a garment. This patent is somewhat removed from more conventional devices, such as the one shown in U.S. Pat. No. 2,504,308 issued to L. Donkle. The Donkle device comprises a blanket having conduits therein which may act either as condensing coils or evaporation coils, depending on the orientation of a valve system with an external compressor. A similar product is depicted in U.S. Pat. No. 2,617,915 issued to G. Blair. Air is passed through a series of "tortuous" channels to provide even inflation. A unique variation of this idea is further shown in U.S. Pat. No. 2,991,627 issued to C. Suits, which discloses the use of Peltier junctions for cooling the person using the blanket. Another invention, described in U.S. Pat. No. 3,867.939 issued to Moore et al., is directed to a layered heating/cooling blanket having an absorbent stratum which may act as an absorbent bandage or be used to apply medicaments. Each of these blankets may be used in a hospital setting in which maintenance of proper body temperature may be critical.

The above-mentioned devices suffer one important drawback—the warm or cool air flowing through the blanket does not come into direct contact with the body, but rather heat transfer must be completed through the blanket material, dissipating the desired effect. This is especially detrimental in the case of small children whose total heat capacity is very low. Some other inventions, however, have overcome this problem by providing a series of air holes in the blanket itself by which the warm or cool air may be directed at the patient. One such invention is shown in U.S. Pat. No. 3,486,177 issued to I. Marshack. In that invention, a permeable cushion is placed over conduits having holes therein; the air flows upwards through the cushion and to the body of the person lying thereon. Obviously, however, the same problem of heat dissipation occurs in the cushion itself. Another version is depicted in U.S. Pat. No. 2,601,189 issued to N. Wales. That blanket utilizes a series of channels which provide uniform distribution of the air; however, the Wales blanket is designed to be placed over the subject, not underneath him, making it useless for surgical procedures since the surgeon must have access to the patient's body. If the Wales blanket is placed underneath the subject, the weight of the body will cut off distribution to the distal ends of the channels. A better design is disclosed in U.S. Pat. No. 2,512,559 issued to A. Williams, in which the two layers of material forming the blanket are spot welded or stitched, whereby the conditioned air may circulate around those portions of the blanket which are compressed due to the weight of the patient's body. Nevertheless, as a practical matter, it has been found that devices such as Williams are not suitable for their intended use because of the tremendous heat loss that occurs in the supplied air between the inlet hose and the distal end of the blanket. In other words, although the air exiting the holes near the inlet port is warm enough to provide heating capability, the temperature of the air exiting the holes which are farther away from the inlet port is close to ambient temperature, which typically has the undesirable effect of actually cooling the patient. If the temperature of the supplied air is raised in order to raise the temperature of the air exiting the distal holes, then the air exiting the proximate holes is so hot as to cause discomfort, and even first degree burns. It would, therefore, be desirable and advantageous to devise a blanket which could warm the body of a patient from underneath, which would overcome the above-identified drawbacks.

SUMMARY OF THE INVENTION

Accordingly, the primary object of the present invention is to provide a blanket which may warm an individual.

Another object of the invention is to provide such a blanket which has a plurality of holes therein providing direct contact between the individual and heated air which is circulated through the blanket.

Yet another object of the invention is to provide such a blanket which may be placed underneath the individual, so that surgical procedures may be performed.

Still another object of the invention is to provide a convection blanket warmer having improved distribution of heat content.

The foregoing objects are achieved in a convection blanket warmer comprising four layers, two inner layers of metallic foil, and two outer layers of a protective, absorbent material. The holes in one side of the blanket are graduated whereby there are fewer holes near the inlet port supplying heated air, and more holes near the end distal from the inlet port. The inlet port is further oriented so that supplied air is directed toward the corner of the blanket most distal from the inlet port.

BRIEF DESCRIPTION OF THE DRAWINGS

The novel features believed characteristic of the invention are set forth in the appended claims. The invention itself, however, as well as a preferred mode of use, further objects and advantages thereof, will best be understood by reference to the following detailed description of illustrative embodiments when read in conjunction with the accompanying drawings, wherein:

FIG. 1 is a perspective view of the convection blanket warmer of the present invention.

FIG. 2 is a cross-sectional view of a portion of the blanket showing the layered arrangement thereof.

FIG. 3 is a top plan view of the convection blanket warmer showing the graduated arrangement of pinholes therein, the intermittent stitching not being shown for clarity.

FIG. 4 is a bottom plan view of the convection blanket warmer depicting the stitching pattern holding the various layers together.

DESCRIPTION OF THE PREFERRED EMBODIMENTS

With reference now to the figures, and in particular with reference to FIG. 1, there is depicted a convection blanket warmer 10. Convection blanket warmer 10 has connected thereto an air supply mechanism 12 by way of hose 14, which may supply either warm or cold air, depending on the needs of the user. Air supply mechanisms are well known in the art, and are described in U.S. Pat. Nos. 2,504,308; 2,512,559; 2,601,189; and 2,617,915, which patents are hereby incorporated for all purposes.

As can more easily be seen in FIG. 2, convection blanket warmer 10 is essentially rectangular, and may vary in size from a small pad of about one foot by two feet, or may be large enough to completely circumscribe an adult patient, i.e., about three feet by seven feet. Of course, convection blanket warmer 10 could appear in shapes other than rectangular but, as it in intended for use on men and women, it will most likely be generally oblong. Air hose 14 enters blanket warmer 10 at a corner 16, a portion of corner 16 being cutout forming an inlet port 18. The cutout in corner 16 is oriented such that the air from hose 14 may be directed to the distal corner 20 of blanket 10, which optimizes air flow within blanket 10.

Hose 14 may be connected to inlet port 18 by any convenient means, such as a drawstring 24 or elastic band which is attached to the circumferential perimeter of inlet port 18. In this manner, the distal end 22 of hose 14 may be inserted into port 18 and drawstring 24 tightened, thereby securing hose 14. The distal end 22 of hose 14 may be supplied with an annular protrusion 26 to better secure hose 14 within port 18. The particular means employed to connect hose 14 to inlet port 18 is not critical and, as those skilled in the art will appreciate, there are a variety of ways to accomplish this. However, it is an object of the present invention to provide an inexpensive convection blanket which may be disposable and, threfore, the use of special fittings attached to inlet port 18 is deemed undesirable by the inventor.

The construction of blanket 10 may best be understood with reference to FIG. 2, a cross-sectional view of blanket 10. There are essentially four layers, a first or top layer 28, a second layer 30, a third layer 32, and a fourth layer 34. Top layer 28 is preferably a cloth-like material. The main requirement for top layer 28 is that it have relatively good insulative properties. The inventor has found a cloth-like textile made from wood pulp suitable for that purpose.

The second layer 30 is affixed to top layer 28 by any suitable means, such as glue or another adhesive. One of the major points of novelty in the present invention lies in the use of a metallic-like ply for second and third layers 30 and 32. It has been found that all of the prior art devices discussed in the Background of the Invention above suffer the extreme disadvantage of losing heat as one progresses from the inlet corner to the corner of the blanket distal from the supply hose. This is simply due to heat transfer through the blanket into the surrounding atmosphere and to the user's body. The inventor has found that use of a metallic-like ply to reflect and contain the heat within blanket 10 has resulted in a remarkable improvement in this regard. Although metal foil would suffice, other insulating materials may be used, such as MYLAR (a trademark for a polyester film). Not only does this minimize the temperature gradient across blanket 10, but it also avoids excessive heating of a patient's body through direct heat transfer. Of course, one of the first or second layers 28 or 30 should be impermeable to air flow. Since, in the preferred embodiment, second layer 30 is an impermeable film of coated MYLAR, it is permissible that first layer 28 be constructed of the above-suggested (air permeable) wood pulp textile.

First and second layers 28 and 30 have a series of pinholes 36 therein (discussed more fully in conjunction with FIG. 3 below), whereby the warmed air may be directed upward through blanket 10. Third and fourth layers 32 and 34 are essentially identical to layers 30 and 28, respectively, except that the lower two layers 32 and 34 have no pinholes. Top layers 28 and 30 are intermittently secured to bottom layers 32 and 34 by means of stitching 38 (discussed more fully in conjunction with FIG. 4 below). All four layers are held together at the edges by seam 40, as more clearly seen in FIGS. 3 and 4.

With reference now to FIG. 3, a top plan view of blanket 10 is depicted, but the stitching 38 has been removed from this view to more clearly depict the novel pinhole pattern of the present invention. A series of pinholes 36 extend along the entire upper surface of blanket 10. As can be clearly seen, the density of holes 36 is greater near distal corner 20 than near proximate corner 16. This pattern, facilitates even distribution of heat along the entire length of blanket 10. As noted above, the air exiting near the distal corner of prior art devices is typically cooler, so the provision of extra ventilation holes at distal corner 20 overcomes this drawback. It should be noted that the pinhole pattern shown in FIG. 3 may be utilized independent of the metallic layering discussed above. However, these two novel features together create the optimum system for a convection blanket warmer.

In FIG. 3, the pinholes become more dense as one moves both laterally and longitudinally away from inlet port 18. In other words, there is a graduated effect going from port 18 toward lateral edge 42, as well as going from port 18 toward longitudinal edge 44. Although this graduation could occur along only one axis, it is contemplated that the pattern set forth in FIG. 3 is optimal. Moreover, it should be realized that a Cartesian system such as that shown in FIG. 3 is not the only generalized pattern; a polar system (not shown) could be used wherein the origin lies at inlet port 18, and the rings of pinholes are closer together as one moves toward distal corner 20. The point is merely to have more air flow near distal corner 20.

To insure that air flow within blanket 10 is uniform, there are no clearly defined channels therein (such as those disclosed in U.S. Pat. Nos. 2,617,915 and 3,867,939). Rather, as can be seen in FIG. 4, stitching 38 occurs intermittently along blanket 10. This is crucial since the weight of the patient's body will compress the layers of blanket 10, which effectively obstructs flow in much of blanket 10. If channeling were present, warm air would be totally unable to reach certain portions of the blanket, contrary to the desired goal of uniform air flow exiting blanket 10. Thus, in the present invention, air may circulate along convulated paths to reach all pinholes 36 which are exposed to the surrounding environment. Of course, some stitching or other affixation is necessary to avoid blowing up the blanket like a balloon.

Although the invention has been described with reference to specific embodiments, this description is not meant to be construed in a limiting sense. Various modifications of the disclosed embodiment, as well as alternative embodiments of the invention will become apparent to persons skilled in the art upon reference to the description of the invention. For example, while the salient features of the present invention are directed to a device for warming persons, the blanket could be used equally well to cool individuals. It is therefore contemplated that the appended claims will cover such modifications that fall within the true scope of the invention.

I claim:

1. A device for distributing air about a person comprising:
   a top layer of insulative material having inner and outer surfaces, and further having a plurality of pinholes therein, said top layer having distal and proximate ends, said pinholes having a larger surface density at said distal end than at said proximate end; and
   a bottom layer of insulative material having inner and outer surfaces, and further having a shape approximately equal to the shape of said top layer, said inner surface of said bottom layer being sealingly attached to said inner surface of said top layer along the peripheries thereof except along a small portion of said peripheries near said proximate end, forming an inlet port at said proximate end for an air supply, whereby air may be forced between said top and bottom layers, exiting through said pinholes;
   a first intermediate layer of metallic foil affixed along its entire surface to said inner surface of said top layer, said first intermediate layer having pinholes therein corresponding to pinholes in said top layer; and
   a second intermediate layer of metallic foil affixed along its entire surface to said inner surface of said bottom layer whereby, when warm air is forced between said first and second intermediate layers, temperature variations of said air along the length of said intermediate layers are minimized;
   said top and bottom layers being further affixed to one another intemittently along their said inner surfaces, thereby preventing the device from becoming overly distended.

2. The device of claim 1 further comprising means for attaching an air supply hose to said inlet port.

3. The device of claim 2 wherein each of said layers has a cutout at said proximate end, said inlet port being located at said cutout, said cutout further being oriented so that said air supply hose directs air toward said distal end.

4. The device of claim 3 wherein said means for attaching said air supply hose comprises a drawstring for encircling a hub on a distal end of said air supply hose.

5. A convection blanket for directing warm air toward a person lying thereon, comprising:
   a first layer of insulative material having inner and outer surfaces, and further having a plurality of pinholes therein;
   a second layer of metallic foil having inner and outer surfaces, said outer surface of said second layer being affixed to said inner surface of said first layer, said second layer having pinholes therein corresponding to pinholes in said first layer;
   a third layer of metallic foil having inner and outer surfaces;
   a fourth layer of insulative material having inner and outer surfaces, said inner surface of said fourth layer being affixed to said outer surface of said third layer; and
   each of said first, second, third and fourth layers being approximately the same size and shape, and being sealingly attached along the peripheries thereof except along a small portion of said peripheries, forming an inlet port at said small portion of said peripheries for an air supply hose, whereby air may be forced between said second and third layers, exiting through said pinholes, and whereby, when warm air is forced between sid second and third layers, temperature variations of said air along the length of the blanket are minimized.

6. The convection blanket of claim 5 having a proximate end at said inlet port, and having a distal end opposite said proximate end, said pinholes having a greater surface density at said distal end than at said proximate end, whereby a larger volume of air passes through said first and second layers at said distal end than at said proximate end.

7. The convection blanket of claim 6 wherein said first, second, third and fourth layers are further affixed to one another intermittently, thereby preventing the blanket from becoming over distended, but allowing air flow around portions thereof which may become obstructed due to the weight of the person lying thereon.

8. The convection blanket of claim 7 wherein each of said layers has a cutout at said proximate end of the blanket, said inlet port being located at said cutout, said cutout further being oriented so that air supply hose directs air toward said distal end.

9. The convection blanket of claim 8 further comprising means for attaching said air supply hose to said inlet port.

10. The convection blanket of claim 9 wherein said means for attaching said air supply hose comprises a drawstring for encircling a hub on a distal end of said air supply hose.

11. A convection blanket for directing warm air toward a person lying thereon, comprising:
    a first layer of insulative material having inner and outer surfaces, and further having a plurality of pinholes therein;
    a second layer of metallic foil having inner and outer surfaces, said outer surface of said second layer being affixed to said inner surface of said first layer, said second layer having pinholes therein corresponding to pinholes in said first layer;
    a third layer of metallic foil having inner and outer surfaces;
    a fourth layer of insulative material having inner and outer surfaces, said inner surface of said fourth layer being affixed to said outer surface of said third layer;
    each of said first, second, third and fourth layers being approximately the same size and being rectangular in shape, forming first, second, third and fourth corners of the blanket, said third corner being opposite said first corner, and being sealingly attached along the peripheries of each of said layers except near said first corner, there being a cutout at said first corner forming an inlet port for an air supply hose, said cutout being oriented whereby said air supply hose is directed toward said third corner;

said first and second layers having a greater surface density of said pinholes moving from said first corner to said third corner;

each of said first, second, third and fourth layers being stitched to one another intermittently, thereby preventing the blanket from becoming overly distended, but allowing air flow around portions thereof which may become obstructed due to the weight of the person lying thereon; and means for attaching said air supply hose to said inlet port.

* * * * *